(12) United States Patent
Tuke et al.

(10) Patent No.: US 6,451,058 B2
(45) Date of Patent: Sep. 17, 2002

(54) PROSTHETIC IMPLANT AND SURGICAL TOOL

(75) Inventors: Michael Antony Tuke, Guildford (GB); Robert Michael Wozencroft, Surbiton (GB); Robert Stephen Parsons, Hanbury (GB)

(73) Assignee: Finsbury (Development) Limited, Surrey (GB)

( * ) Notice: Subject to any disclaimer, the term of this patent is extended or adjusted under 35 U.S.C. 154(b) by 0 days.

(21) Appl. No.: 09/342,857

(22) Filed: Jun. 29, 1999

Related U.S. Application Data
(60) Provisional application No. 60/139,664, filed on Jun. 17, 1999.

(51) Int. Cl.[7] ............................................. A61E 2/32
(52) U.S. Cl. ................................................. 623/22.21
(58) Field of Search ........................... 623/22, 22.21, 623/22.23, 22.24, 22.25, 22.28, 22.31, 22.32, 22.34, 22.38, 23.43, 23.5, 22.15

(56) References Cited

U.S. PATENT DOCUMENTS

| | | | | |
|---|---|---|---|---|
| 3,067,740 A | * | 12/1962 | Haboush ................. | 623/22.15 |
| 3,584,318 A | * | 6/1971 | Scales et al. ............ | 623/22.21 |
| 3,745,590 A | * | 7/1973 | Stubstad ................. | 623/13.11 |
| 3,909,855 A | * | 10/1975 | Barredo .................. | 623/32 |
| 4,180,873 A | * | 1/1980 | Fixel ..................... | 623/22.23 |
| 4,244,060 A | * | 1/1981 | Hoffer ................... | 623/6.15 |
| 4,961,748 A | * | 10/1990 | Frey et al. .............. | 623/22.21 |
| 5,108,447 A | * | 4/1992 | Zeiler et al. ............ | 623/22.21 |
| 5,376,126 A | * | 12/1994 | Lin ....................... | 623/23.11 |
| 5,534,011 A | * | 7/1996 | Greene, Jr. et al. ...... | 606/232 |
| 5,549,692 A | * | 8/1996 | Hauser et al. .......... | 623/22.21 |
| 5,702,476 A | * | 12/1997 | Limacher et al. ........ | 623/22.28 |
| 5,702,477 A | * | 12/1997 | Capello et al. .......... | 623/22.21 |
| 5,873,906 A | * | 2/1999 | Lau et al. ............... | 606/198 |
| 5,931,870 A | * | 8/1999 | Cuckler et al. .......... | 623/22.21 |

FOREIGN PATENT DOCUMENTS

DE         3324103    * 11/1984        ................. 623/22

\* cited by examiner

*Primary Examiner*—Eduardo C. Robert
(74) *Attorney, Agent, or Firm*—Senniger, Powers, Leavitt & Roedel

(57) ABSTRACT

The invention relates to a prosthetic implant comprising a main body portion having a first surface for presentation to a receptive bone surface or into a bone cavity and a second surface for receipt of an articulating joint, and a lug on, and/or a bore in, the main body portion of the implant which is adapted for attachment of a filamentary member, such as a cable. The invention also relates to a surgical tool for gripping the implant, comprising an elongate body having a first end surface for bearing on the prosthetic implant and adapted for attachment of the tool to the implant, directly or indirectly by means of the cable.

65 Claims, 10 Drawing Sheets

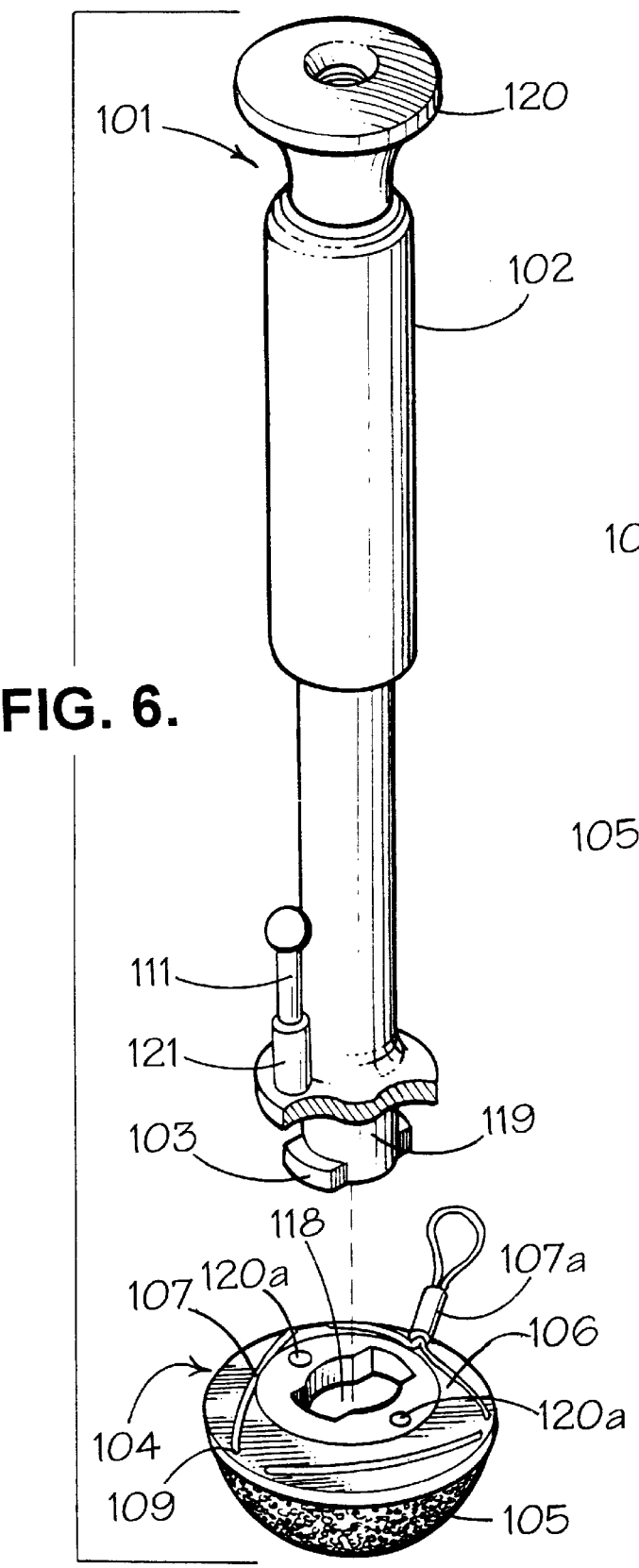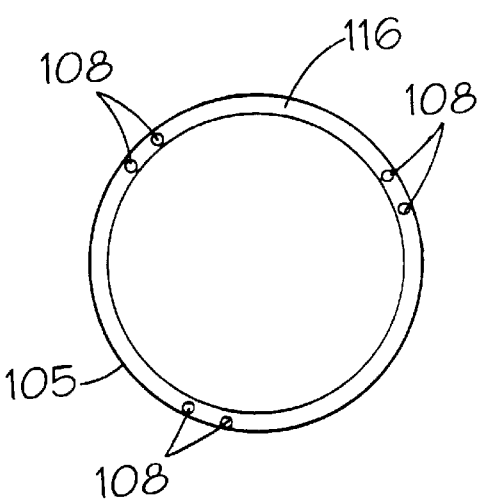

PROSTHETIC IMPLANT AND SURGICAL TOOL

This application claims priority from Provisional application Ser. No. 60/139,664, filed Jun. 17, 1999.

FIELD OF THE INVENTION

The present invention relates to a prosthetic implant and to a surgical tool for gripping the prosthetic implant during a surgical procedure.

BACKGROUND OF THE INVENTION

The replacement of all or a part of the bone surface of an articulation with a prosthetic implant has become a common surgical procedure. The procedure requires the surgeon to exercise both precision and delicacy in the placement of the prosthetic implant. However, it is frequently necessary for the surgeon also to exercise a degree of force, sometimes a vigorous force, in order to situate the prosthetic implant in a desired location on the bone surface.

For example, in an operation to insert a prosthetic acetabulum in a patient's pelvis the surgeon first uses a reamer to grind a cavity of appropriate size in the patient's pelvis. The surgeon then inserts an acetabular cup into the cavity. By "appropriate size" is meant a size which is selected by the surgeon as being the most appropriate for that particular patient. Normally, it is desirable to retain as much of the original healthy bone surface as possible.

Commercially available acetabular cups are sold in a range of sizes to suit the needs of individual patients. Generally, acetabular cups are available in sizes of from 42 mm to 62 mm diameter, with 2 mm increments between neighbouring sizes.

Prosthetic acetabular cups generally require the use of an insertion tool to achieve correct positioning of the prosthesis in the patient's pelvic cavity. A typical insertion tool is described in U.S. Pat. No. 4,305,394 (Bertuck).

There are a number of different types of prosthetic acetabular cups. Firstly, cups made from polyethylene are available. Polyethylene cups are cemented into the acetabulum and require only light pressure to seat them in the cement. Secondly, there are cups which comprise a metal shell for insertion into the pelvic cavity and a polyethylene liner for articulation with the femur. Some polyethylene cups with metal shells are implanted without cement and rely on a jam fit between the metal shell and the patient's acetabulum. Often these metal shells have surfaces or coatings which encourage bone to grow into them over time. A typical coating material is hydroxyapatite. With this type of prosthesis, the polyethylene liner is snapped or screwed into the metal shell after the metal shell has been seated in the acetabulum to form the socket part of the patient's joint.

Cups which rely on a jam fit require a greater force to be applied via the insertion tool than is the case with cemented polyethylene cups. This force is usually applied as a direct impact into the acetabulum, for example by use of a mallet on the free end of the insertion tool. However, it may also be necessary to adjust the angular position of the cup in the bone or to take it out if positioned incorrectly. Therefore the insertion tool must positively grip the cup by some mechanical feature. This feature cannot impinge upon the outside of the metal shell because the insertion tool may then become trapped between the shell and the bone. Also there is little room around the rim of the shell because the wall thickness of the shell is generally kept to a minimum. Therefore the insertion tool usually grips on a mechanical feature on the inner hemisphere of the metal shell. An insertion tool of this type is described in International Patent Publication No. WO 94/21199 (Howmedica Limited). The mechanical feature is usually designed so as to cause minimum compromise to the function of the prosthetic hip joint. As a result it is often not strong enough for the impaction forces applied. This often results in damage to the insertion tool, or metal shell or both.

A third category of prosthetic hip joint exists which is manufactured entirely from metal so that the prosthetic articulation comprises a metal on metal joint. These are nearly always implanted without cement, relying on a jam fit in the acetabulum. With this type of cup the inner hemisphere is not a convenient place to locate a mechanical feature for the insertion tool to grip on. First, it would reduce the surface area of the prosthetic articulation. Secondly, it could cause damage to the highly polished concave metal against which the ball of the patient's femur or the ball head of a femoral prosthesis is to bear.

Therefore, the provision of means for attaching an insertion tool to a prosthetic implant so that the attachment is sufficiently robust to withstand the impaction and other forces to which it may be subject during insertion of the prosthesis and yet which does not compromise the structural strength or the articulating properties of the prosthesis itself remains a problem in the art.

Another disadvantage of conventional tools is that they must be manufactured in a range of different sizes to receive acetabular cups or sheaths of the different sizes referred to above.

The difficulty of gripping and positioning prosthetic implants applies not only to acetabular implants but more generally to implants such as the tibial and femoral components of a prosthetic knee.

U.S. Pat. No. 5,376,126 (Lin) discloses use of cords to assist in fastening a femoral implant to the upper end of a resected femur.

SUMMARY OF THE INVENTION

It is an object of the present invention to provide a prosthetic implant which does not suffer from one or more of the disadvantages of the prior art devices. It is further an object of the present invention to provide a surgical tool for use with such an implant.

Accordingly, the present invention provides a prosthetic implant comprising a main body portion, having a first surface for presentation to a receptive bone surface or to a surgically prepared bone cavity and a second surface for receipt of an articulating joint, and filamentary member attachment means adapted for attachment of a filamentary member to the implant.

The filamentary member can be a monofilamentary member, such as a Kevlar™ monofilament, or a multifilament member such as a Kevlar™ polyfilamentary thread or a metallic cable made, for example, from stainless steel. Such a cable may be, for example, from about 0.5 mm thick to about 2 mm thick. If desired, the cable can be coated with an inert material, such as polypropylene. Preferably the filamentary member is formed into a closed loop.

In one form of prosthetic implant according to the invention the filamentary member attachment means comprises a lug on the main body portion around which a filamentary member can be looped. Alternatively the filamentary member attachment means can comprise a bore in the main body portion through which a filamentary member can be threaded. In such a case it will normally be preferred to provide plurality of such bores, for example, three such bores.

The invention further provides such a prosthetic implant further comprising a cable attached to the main body portion of the implant by the filamentary member attachment means. Thus in a preferred embodiment of the invention the filamentary member attachment means comprises a plurality of bores in the main body portion and a filamentary member is threaded through each of the plurality of bores in turn, the free ends of the filamentary member being secured one to another so as to form a closed loop of filamentary member. The free ends of the filamentary member can be secured to one another by means of a sleeve having first and second ends, the sleeve snugly receiving a first looped portion of filamentary member located near a first end portion of the filamentary member and inserted from the first end of the sleeve so as to project as a first loop from the second end of the sleeve with the first end portion being passed through the first loop, and the sleeve further snugly receiving a second looped portion of filamentary member located near a second end portion of the filamentary member and inserted from the second end of the sleeve so as to project as a second loop from the first end of the sleeve with the second end portion being passed through the second loop, whereby upon tension being applied to the closed loop of filamentary member the first and second end portions of the filamentary member are firmly gripped by the first and second loops respectively.

The invention also provides an acetabular hip prosthesis for implantation in a surgically prepared socket in a hip of a patient comprising:

a generally cup-shaped body having:

an outer generally convex surface for contact with bone of a surgically prepared socket in a hip of a patient;

an inner generally concave surface;

a peripheral bridge portion whose surface extends between the outer generally convex surface and the inner generally concave surface; and at least one bore which extends from a first opening in the surface of the bridge portion through an interior portion of the substantially cup-shaped body to a second opening in the surface of the bridge portion, the bore being adapted for receipt of a filamentary member therethrough for holding the prosthesis on the end of an insertion tool to facilitate insertion of the prosthesis into the prepared socket.

In such an acetabular hip prosthesis there is preferably provided a plurality of bores each of which extends from a first opening in the surface of the bridge portion through an interior portion of the substantially cup-shaped body to a second opening in the surface of the bridge portion, the bore being adapted for receipt of a filamentary member therethrough for holding the prosthesis on the end of an insertion tool to facilitate insertion of the prosthesis into the prepared socket.

Preferably the outer generally convex surface of the cup-shaped body is provided with a coating of hydroxyapatite and also is texturised to facilitate ingrowth of bone after implantation into a surgically prepared hip socket of a patient.

In another aspect of the invention there is provided a protected prosthetic implant comprising a main body portion, having a first surface for presentation to a receptive bone surface and a second surface for receipt of an articulating joint, filamentary member attachment means adapted for attachment of a filamentary member to the implant, and a protective cap for covering at least part of the second surface of the main body portion of the implant. The protective cap can be attached to the main body portion of the implant by means of a cable. In this case the cable can be tensioned so that the protective cap is tightly attached to the main body portion of the implant.

The protective cap is preferably made of a rigid material. It can be provided with a number of holes, through which the filamentary member is threaded for attachment of the protective cap to the prosthetic implant.

It will often be preferred for the protective cap to be a disposable protective cap. Alternatively it can be reusable after appropriate sterilisation.

The invention further provides a protected acetabular hip prosthesis for implantation in a surgically prepared socket in a hip of a patient comprising:

(i) a generally cup-shaped metal body having:

an outer generally convex surface for contact with bone of a surgically prepared socket in a hip of a patient;

an inner substantially part spherical cavity in the metal body, the cavity having a generally concave polished surface for receipt of a ball head on a femoral prosthesis and a periphery surrounding the cavity and defining a mouth;

a peripheral bridge portion whose surface extends between the periphery of the cavity and the outer generally convex surface; and at least one bore which extends from a first opening in the surface of the peripheral bridge portion through an interior portion of the substantially part spherical body to a second opening in the surface of the bridge portion, the at least one bore being adapted for receipt of a filamentary member therethrough for holding the prosthesis on the end of an insertion tool to facilitate insertion of the prosthesis into the surgically prepared socket;

(ii) a cover member adapted to bridge the cavity, the cover having apertures therethrough which correspond to the first and second openings in the metal body and are adapted for passage of the filamentary member; and (iii) a filamentary member threaded through the at least one hole in the metal body and through the apertures in the cover member, the free ends of the filamentary member being secured one to another to form a closed loop of filamentary member which secures the cover to the metal body.

Yet again the invention provides a protected acetabular hip prosthesis for implantation in a surgically prepared socket in a hip of a patient comprising:

(i) a generally cup-shaped metal body having:

an outer generally convex surface for contact with bone of a surgically prepared socket in a hip of a patient;

an inner substantially part spherical cavity in the metal body, the cavity having a generally concave polished surface for receipt of a ball head on a femoral prosthesis and a periphery surrounding the cavity and defining a mouth;

a peripheral bridge portion whose surface extends between the periphery of the cavity and the outer generally convex surface; and a plurality of bores each of which extends from a first opening in the surface of the peripheral bridge portion through an interior portion of the substantially part spherical body to a second opening in the surface of the bridge portion, the bores being adapted for receipt of a filamentary member therethrough for holding the prosthesis on the end of an insertion tool to facilitate insertion of the prosthesis into the surgically prepared socket;

(ii) a cover member adapted to bridge the cavity, the cover having apertures therethrough which correspond to the first and second openings in the metal body and are adapted for passage of the filamentary member ; and (iii) a filamentary member threaded through each of the plurality of holes in the metal body and through the apertures in the cover member, the free ends of the filamentary member being secured one to another to form a closed loop of filamentary member which secures the cover to the metal body.

In addition, the invention provides a protected acetabular hip prosthesis for implantation in a surgically prepared socket in a hip of a patient comprising:

(i) a generally cup-shaped metal body having:

an outer generally convex surface for contact with bone of a surgically prepared socket in a hip of a patient;

a cavity in the metal body for receipt of a liner of plastics material, the cavity having a periphery surrounding the cavity and defining a mouth;

a peripheral bridge portion whose surface extends between the periphery of the cavity and the outer generally convex surface; and a plurality of bores each of which extends from a first opening in the surface of the peripheral bridge portion through an interior portion of the substantially part spherical body to a second opening in the surface of the bridge portion, the bores being adapted for receipt of a filamentary member therethrough for holding the prosthesis on the end of an insertion tool to facilitate insertion of the prosthesis into the surgically prepared socket;

(ii) a liner of plastics material secured in the cavity of the cup shaped metal body, the liner having an outer surface adapted to conform to the inner surface of the cavity in the cup-shaped metal body and a substantially part spherical inner surface for receipt of a ball head on a femoral hip prosthesis;

(iii) a cover member having a first face adapted to bridge the cavity, the cover member having apertures therethrough which correspond to the first and second openings in the metal body and are adapted for passage of the filamentary member ; and (iv) a filamentary member threaded through each of the plurality of holes in the metal body and through the apertures in the cover member, the free ends of the filamentary member being secured one to another to form a closed loop of filamentary member which secures the cover to the metal body.

Preferably the cavity in the cup-shaped metal body is provided with an inwardly projecting lip surrounding the mouth of the cavity and the liner is provided with a peripheral ledge which is adapted to snap fit under the inwardly projecting lip of the cup-shaped metal body. It will also often be preferred that the cavity in the cup-shaped metal body is provided with a circumferential internal ridge below and adjacent the inwardly projecting lip and wherein the liner is provided with a corresponding circumferential groove on its outer surface which is adapted to receive the circumferential ridge. It will further often be desirable for the liner to be is made from high density polyethylene. In one particularly preferred form of the invention the cover member is provided on a second face opposite its first face with an axial blind bore for location of a corresponding axial locating peg on an insertion tool. In addition the cover member can be provided on its second face with an auxiliary bore whose axis is parallel to and offset from the axis of the axial blind bore, the auxiliary bore being adapted to receive a corresponding offset peg on an insertion tool to prevent relative rotation of the acetabular hip prosthesis and cover member about the axis of the axial locating peg of the insertion tool.

In another aspect of the invention there is provided a surgical tool for gripping a protected acetabular hip prosthesis for implantation in a surgically prepared socket in a hip of a patient, the protected acetabular hip prosthesis comprising a generally cup-shaped metal body which has an outer generally convex surface and a cavity defining a mouth, a protective cap over the mouth of the cavity, and a closed loop of filamentary member secured to the acetabular hip prothesis, the tool comprising an elongated body having a first end for engagement with the protective cap and adjustable filamentary member engagement means for engagement with and tightening of the closed loop of filamentary member so as to locate the protective cap against the first end of the tool and to draw the acetubular hip prosthesis towards the first end surface thereby to hold the prosthetic implant securely on the first end of the tool during surgical implantation of the acetabular hip prothesis, the tool and protective cap being removable after such surgical implantation by loosening the tension in the closed loop of filamentary member and then severing the closed loop of filamentary member to allow it to be disengaged from the implanted acetabular hip prosthesis.

Also provided in accordance with the invention is a surgical tool for gripping the prosthetic implant of the invention, comprising an elongate body having a first end surface for bearing on the implant and means on the tool adapted for attachment thereto of a cable from the implant.

The attachment of the tool to the prosthetic implant is achieved by means of a filamentary member, such as a cable. The attachment may be a direct attachment, in which case a cable is passed between the implant and the tool and secured to each by the respective attachment means. The attachment may be an indirect attachment, by which is meant that the cable may be used to attach a protective cover to the prosthetic implant and the tool may then be attached to the protective cover. Embodiments of the invention which make use of this indirect attachment will be described in more detail below.

The filamentary member attachment means on the prosthetic implant may comprise a lug on the main body portion of the implant around which a cable or other filamentary member can be looped. Alternatively, or also, the filamentary member attachment means may comprise a bore in the main body portion of the implant through which a cable can be threaded.

The adjustable filamentary member attachment means on the tool may comprise a mooring peg on the tool. The mooring peg may be mounted on a carriage which is movable axially within the body of the tool to tension the cable. Alternatively the adjustable filamentary member attachment means on the tool may comprise a spring loaded arm on the tool. The arm may be mounted on a carriage which is movable axially within the body of the tool to tension the cable or other filamentary member.

The cable or other filamentary member may be an endless cable which may be looped around or threaded through the filamentary member attachment means. Alternatively, a length of cable may be used and secured to each filamentary member attachment means by any convenient means, such as a tie, clip, or knot. Any convenient number of cables or other filamentary members may be used and any convenient number of attachment means on the prosthetic implant and on the surgical tool may be employed. For example, in one preferred embodiment of the invention, the prosthetic implant is an acetabular cup comprising three means. Each filamentary member attachment means is preferably spaced evenly from an adjacent filamentary member attachment means around the rim of the cup. The surgical tool may also comprise three adjustable filamentary member attachment means. Each of these adjustable filamentary member attachment means is preferably spaced evenly around the circumference of the tool from an adjacent filamentary member attachment means. The filamentary member is preferably an endless stainless steel cable which passes from a first filamentary member attachment means on the cup to a first corresponding adjustable filamentary member attachment means on the tool and then on to successive respective second and third attachment means on the implant and on the tool, returning in an endless loop to the first filamentary member attachment means on the cup.

The surgical tool and prosthetic implant of the invention have a number of significant advantages over the prior art. The use of a cable or other filamentary member to provide, directly or indirectly, means for securing the implant to the insertion tool means that any compromise in the structural and functional integrity of the implant as a result of the attachment is minimised. The diameter of the cable may be quite small, for example from about 0.5 mm to about 2 mm, and the means for attachment of the cable to the implant may be correspondingly small. For example, a bore of from about 0.5 mm to about 2 mm in the rim of a prosthetic acetabulum of cobalt chrome will not compromise the strength of the implant to any serious degree. Similarly, the provision of lugs having sufficient protrusion to allow a cable of from about 0.5 mm to about 2 mm diameter to be looped therearound on the outer surface of the acetabulum, adjacent the rim thereof, will not interfere to any serious degree with the positioning of the implant in the bone cavity.

The use of a cable or other filamentary member to secure the implant to the tool also has the advantage that the visibility of the attachment area by the surgeon is maintained at a significantly high degree. It is often important for the surgeon to be able to see clearly the position of the implant with respect to the bone surface or cavity.

The surgical tool of the invention may further be provided with means for tensioning the cable or other filamentary member after attachment of the cable to the tool to bring the first end surface of the tool to bear upon the implant. For example, the first end surface of the tool may comprise one or more flanges for bearing on the rim of an acetabular cup. The adjustable filamentary member attachment means on the tool may comprise one or more mooring pegs on the tool, the or each mooring peg being mounted on a carriage which is movable axially within the body of the tool to tension the cable. Alternatively the adjustable filamentary member attachment means on the tool may comprise a spring loaded arm on the tool, the or each arm being mounted on said carriage. Preferably, the carriage is carried on a screw-threaded member mounted axially within the body.

When used, the protective cover may be a disposable protective cover, or it may be reusable after appropriate sterilisation. The protective cover is preferably of a rigid material, for example polyethylene. Preferably, the protective cover is provided with a number of holes, through which the cable is threaded for attachment to the main body portion of the prosthetic implant. The main body portion of the prosthetic implant may comprise one or more lugs, around which the cable may be looped for attachment of the main body portion to the protective cover by means of the cable. Alternatively, or also, the main body portion of the prosthetic implant may be provided with one or more bores through which the cable may be threaded for attachment of the main body portion to the protective cover by means of the cable.

The means for attachment of the tool to the protective cover may comprise a shaped plug on one end of the tool, the plug being receivable within a corresponding socket provided on the protective cover. Preferably, a biased locating pin is provided on the tool, the pin being locatable within a corresponding opening provided on the protective cover, the biasing urging the pin into the opening to prevent rotation between the insertion tool and the implant so that rotational forces can be applied to the implant by means of the tool when the implant is positioned or impacted.

Alternatively, or also, the means for attachment of the tool to the protective cover may comprise means on the tool for attachment of the cable thereto. In this case, there may further be provided means for tensioning the cable after attachment of the cable to the tool to bring the first end surface of the tool to bear upon the protective cover. The means on the tool for attachment of the cable may comprise one or more mooring pegs on the tool, the or each mooring peg being mounted on a carriage which is movable axially within the body of the tool to tension the cable. Alternatively the means for attachment of the cable may comprise one or more spring loaded arms being mounted on said carriage. Preferably, the carriage is carried on a screw-threaded member mounted axially within the body.

When a protective cover is used in the implant of the invention, there is no necessity to manufacture surgical tools of different sizes to correspond to different sizes of acetabular cup or sheath. It is sufficient that the protective cover comprise a receiving area for the surgical tool. When a tensioned cable is used to grip the prosthetic implant the attachment provided is robust in lateral and axial directions, whilst allowing the surgeon to retain good visibility of the implant during the surgical procedure.

When a tensioned cable is used to effect direct attachment between the implant and the tool, the surgeon is allowed not only a good degree of rotational and axial control over the implant whilst inserting the implant, but also the surgeon is able to extract the implant if he is not satisfied with its orientation after initial insertion.

When any of the embodiments of the invention are applied to the implantation of a prosthetic acetabular cup comprising a polyethylene unit and a metal shell, it is not necessary for the polyethylene liner unit to be snapped or screwed into the metal shell after it has been seated in the acetabulum. A result of this is that the polyethylene liner unit may be factory fitted reducing the risk of damage to the unit during fitting.

BRIEF DESCRIPTION OF THE DRAWINGS

FIG. 6 shows an isometric, partly cut away view of a second form of surgical tool and a second assembled and protected prosthetic implant according to the invention.

FIG. 7 shows a plan view from above of the main body portion of the prosthetic implant of FIG. 6 when disassembled from its disposable protective cover.

DESCRIPTION OF THE PREFERRED EMBODIMENTS

Figure 1:
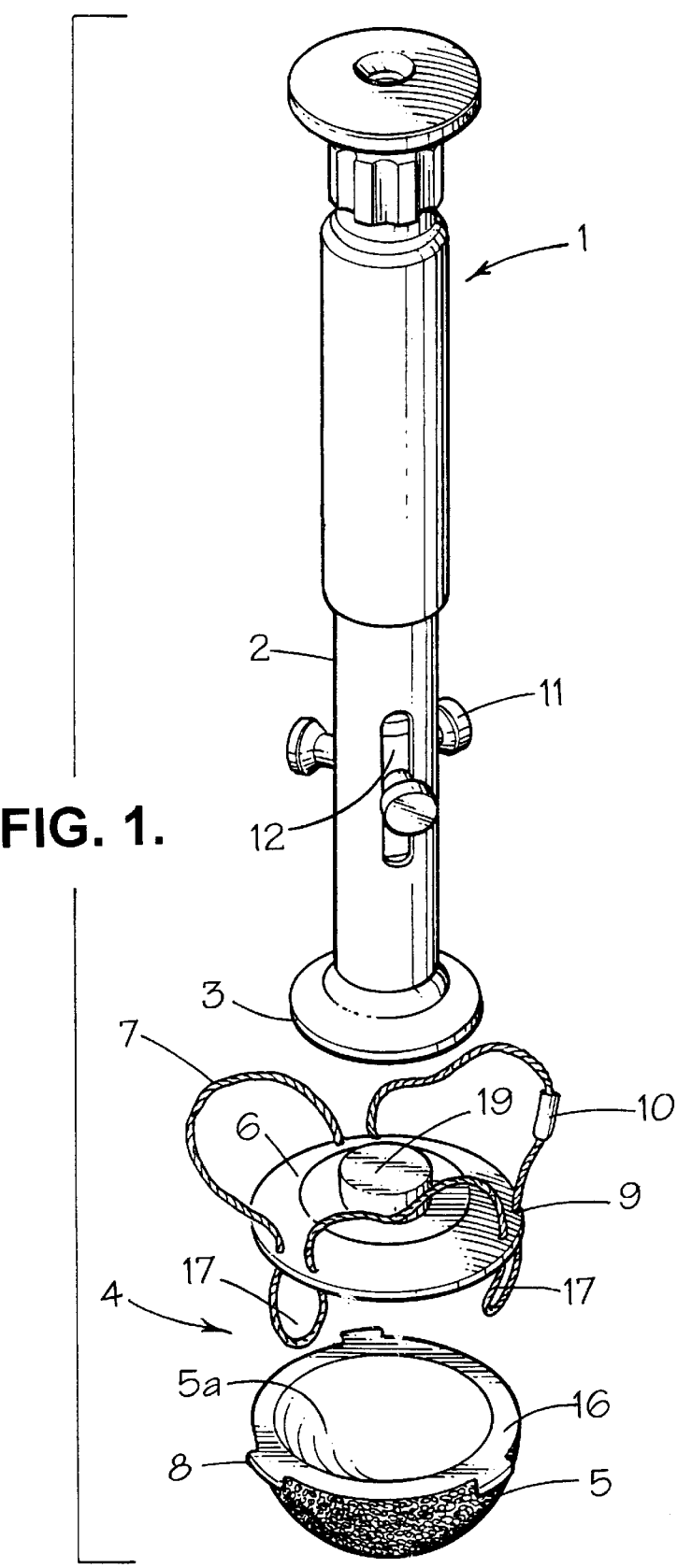
FIG. 1 shows an isometric view of a first form of surgical tool and, in disassembled state, a first prosthetic implant in accordance with the invention and a protective cover therefor.

Referring to FIG. 1, there is shown a surgical tool 1 having an elongate body 2 and a first end surface 3 for bearing on a prosthetic implant 4.

Prosthetic implant 4 comprises a main body portion 5 which is an acetabular cup manufactured from cobalt chrome and intended for use as part of a metal on metal articulating joint. The inner articulating surface 5a of acetabular cup 5 is highly polished and is covered (when the implant is assembled in readiness for implantation in a prepared acetabular socket of a patient) by a disposable protective cover 6 which is manufactured from a plastics material such as polyethylene.

As will be apparent from the foregoing description, the provision of a disposable protective cover is a preferred feature of the invention. With the tool and prosthetic implant depicted in FIG. 1, the disposable protective cover 6 may, if desired, be omitted. In this case, end surface 3 of tool 1 would be provided with one or more flanges (not shown), or would itself be of sufficient diameter, to bear directly on the rim of acetabular cup 5 when assembled.

When prosthetic implant 4 is assembled in readiness for implantation, a cable 7 secures disposable protective cover 6 to acetabular cup 5 by means of lugs 8 on acetabular cup 5 and holes 9 through disposable protective cover 6.

Cable 7 is made of stainless steel. However, any suitable material, such as a suitable synthetic fibre, may be used for manufacture of the cable 7. The cable may be a continuous cable, as is shown in FIG. 1. Compression clip 10 secures the two free ends of cable 7 together in the prosthetic implant of FIG. 1. Alternatively, cable 7 may be formed from a series of individual loops or lengths of cable.

In the embodiment of the invention shown in FIG. 1, three cable loops are depicted. It will be readily understood by those skilled in the art that any other practical number of cable loops (e.g. 4, 5 or 6) could alternatively be used.

Tool 1 comprises mooring pegs 11 for attachment of cable 7. Mooring pegs 11 are movably mounted in slots 12 on elongate body 2.

Figure 2:
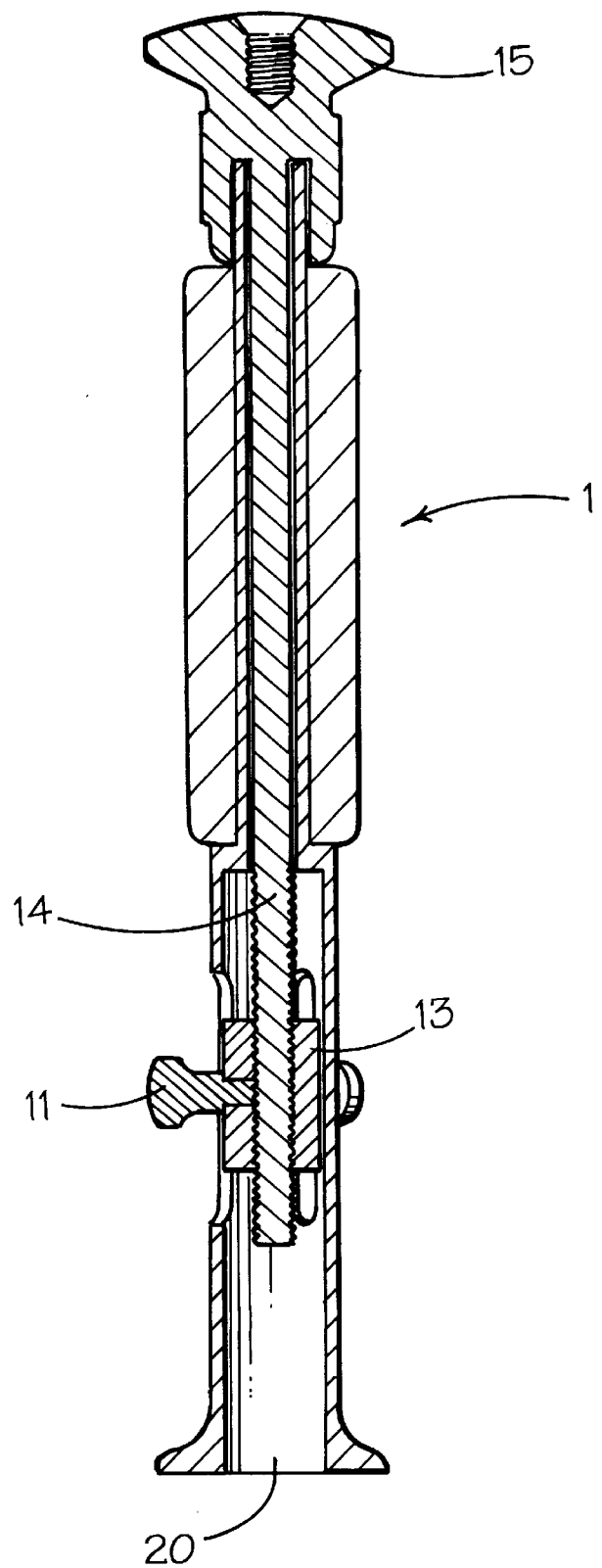
FIG. 2 shows a cross-section along the axis of the surgical tool of FIG. 1.

Referring to FIG. 2, it can be seen that mooring pegs 11 are mounted on a carriage 13 which is carried on screw-threaded member 14. By rotating knob 15 at the top of tool 1, carriage 13 can be made to move up or down from its intermediate position, i.e. the position shown in FIG. 1.

Figure 3:
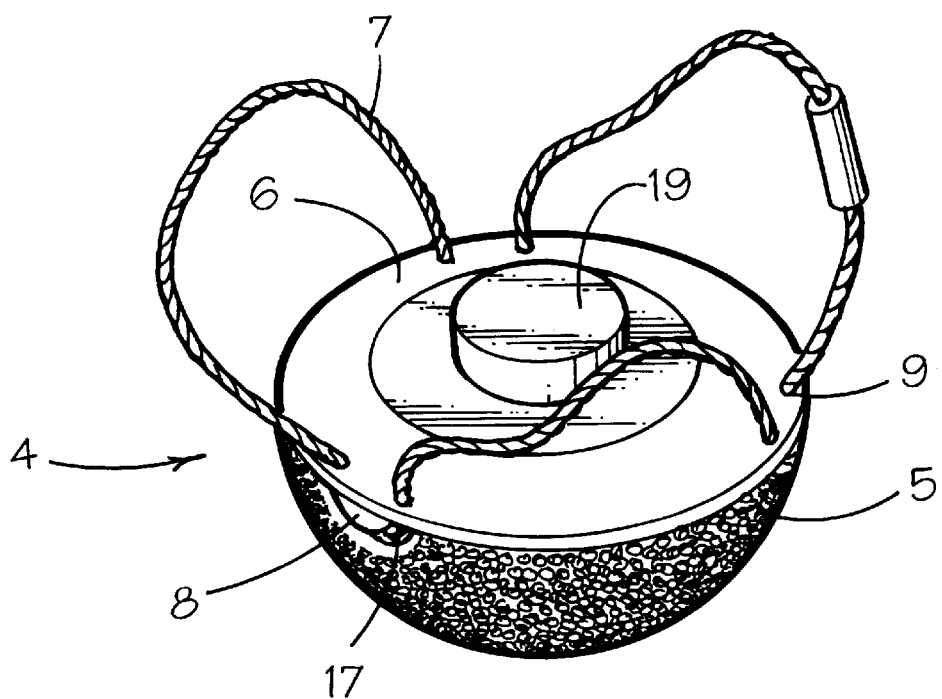
FIG. 3 shows an isometric view of the prosthetic implant of FIG. 1 and its protective cover when assembled.

FIG. 3 shows prosthetic implant 4 when assembled with its protective cover 6 held in place by means of cable 7 so as protect polished surface 5A. It is intended that the implant 4 will be supplied to customers in assembled form. However, implant 4 may alternatively be assembled by a surgeon about to use it. Disposable protective cover 6 is placed over the rim of acetabular cup 5 and each respective loop 17 of cable 7 is hooked over a respective lug 8 of acetabular cup 5. The disposable protective cover 6 is secured to acetabular cup 5 by drawing cable 7 through holes 9 so as to tighten each loop 17 around its respective lug 8. Disposable protective cover 6 has on its uppermost surface a raised portion or peg 19 which is receivable within a corresponding cavity 20 in the body 2 of tool 1. Disposable protective cover 6 may further have on its underside, in the orientation depicted, a peripheral portion of reduced thickness surrounding a downwardly projecting portion for receipt within the rim 16 of acetabular cup 5, but this is not shown in the drawings.

Figures 4, 5:
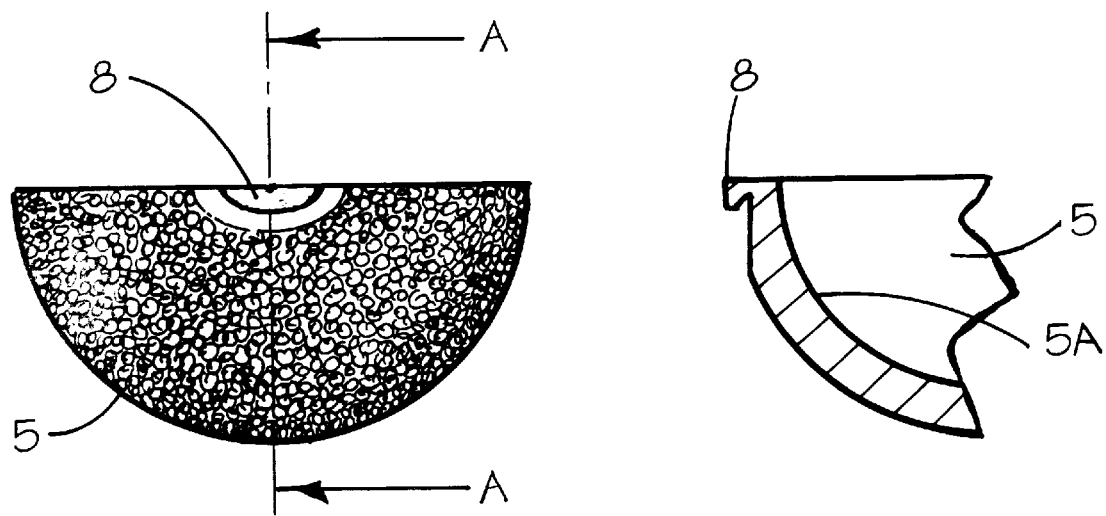
FIG. 4 shows a side view of the main body portion of the prosthetic implant of FIGS. 1 and 3.
FIG. 5 shows a partial cross-section on line A—A of FIG. 4.

FIG. 4 shows a side view of the acetabular cup 5 and one of the lugs 8. FIG. 5 is a cross-section on line A—A of FIG. 4 and shows lug 8 on acetabular cup 5.

Referring back now to FIGS. 1, 2 and 3, in use of the tool 1, the surgeon will attach the assembled prosthetic implant 4 to the tool 1 simply by bringing the disposable protective cover 6 into contact with the end surface 3 of tool 1, so that raised portion or peg 19 is received within cavity 20, and looping each respective loop of cable 7 around each respective receiving mooring peg 11. Rotation of knob 15 in a clockwise direction causes carriage 13 to slide upwardly and tension each loop of cable 7.

Once the prosthetic implant 4 is securely attached to the tool 1, the surgeon may then insert the prosthetic implant 4 into a surgically prepared acetabular cavity in a hip of the patient upon whom the surgical operation is being performed. When the prosthetic implant 4 is located to the surgeon's satisfaction, he simply rotates knob 15 in an anti-clockwise direction to release the tension on cable 7. He then unloops cable 7 from mooring pegs 11 and withdraws tool 1 from the operating area.

To detach disposal protective cover 6 and cable 7 from acetabular cup 5, the surgeon may either unhook the cable 7 from each lug 8 of acetabular cup 5 or he may simply cut cable 7 and pull the cut cable through the holes 9 of disposable protective cover 6.

Referring now to FIG. 6, there is shown a second form of surgical tool 101 having an elongate body 102 and a first end portion 103 for engagement with a prosthetic implant 104.

Prosthetic implant 104 comprises a main body portion 105 which is an acetabular cup manufactured from cobalt chrome and intended for use as part of a metal on metal articulating joint. The articulating surface of acetabular cup 105 is covered by a disposable protective cover 106 which is manufactured from a suitable plastics material, such as polyethylene.

A cable 107 secures disposable protective cover 106 to acetabular cup 105 by means of tunnels 108 in the rim 116 of acetabular cup 105 and holes 109 through disposable protective cover 106. Tunnels 108 cannot be seen in FIG. 6 but their ends are visible in FIG. 7, which shows a plan view of the acetabular cup component 105 of prosthetic implant 104. Each tunnel 108 follows a roughly C-shaped path extends the short distance between a corresponding pair of adjacent pair of adjacent tunnel ends as illustrated in FIG. 7.

Cable 107 is tensioned by means of a clip 107a to ensure tight registry between protective cover 106 and cup 105.

Referring back to FIG. 6, the first end portion 103 is shaped to fit through a corresponding aperture 118 in disposable protective cover 106 and so that it can then be rotated through a quarter turn so as to secure tool 101 to protective cover 106 in bayonet and socket fashion. First end portion 103 is located on the end of a barrel 119 which is rotatable inside elongate body 102 by means of knob 120. Locating pin 111 is provided to secure tool 101 with respect to the disposable protective cover 106 and is receivable within either of corresponding openings 120a in disposable protective cover 106. Pin 111 is retractable from opening 120 by manual pressure applied to lift pin 111 towards its retracted position. Pin 111 is biased towards its unretracted position by means of a coil spring (not shown) housed within chamber 121.

In use of the tool 101, the surgeon will attach the assembled prosthetic implant 104 to the tool 1 simply by passing the end portion 103 through socket 118 of disposable protective cover 106 and rotating the barrel 119 of tool 101 through a quarter turn using knob 120 so that the tool 101 is secured to the prosthetic implant 104 by means of the bayonet and socket action. Then biased locating pin 111 can be caused to snap into a corresponding one of the openings 120a.

Once the prosthetic implant 104 is securely attached to the tool 101, the surgeon may then insert the prosthetic implant 104 into a surgically prepared acetabular cavity of the patient. When the prosthetic implant 104 is located to the surgeon's satisfaction, he simply pulls locating pin 111 upwardly to release it from opening 120 and rotates elongate body 102 by a quarter turn before withdrawing tool 101 from the operating area.

To detach disposal protective cover 106 and cable 107 from acetabular cup 105, the surgeon must cut cable 107 and pull the cut cable through the holes 109 of disposable protective cover 106.

Figure 8:
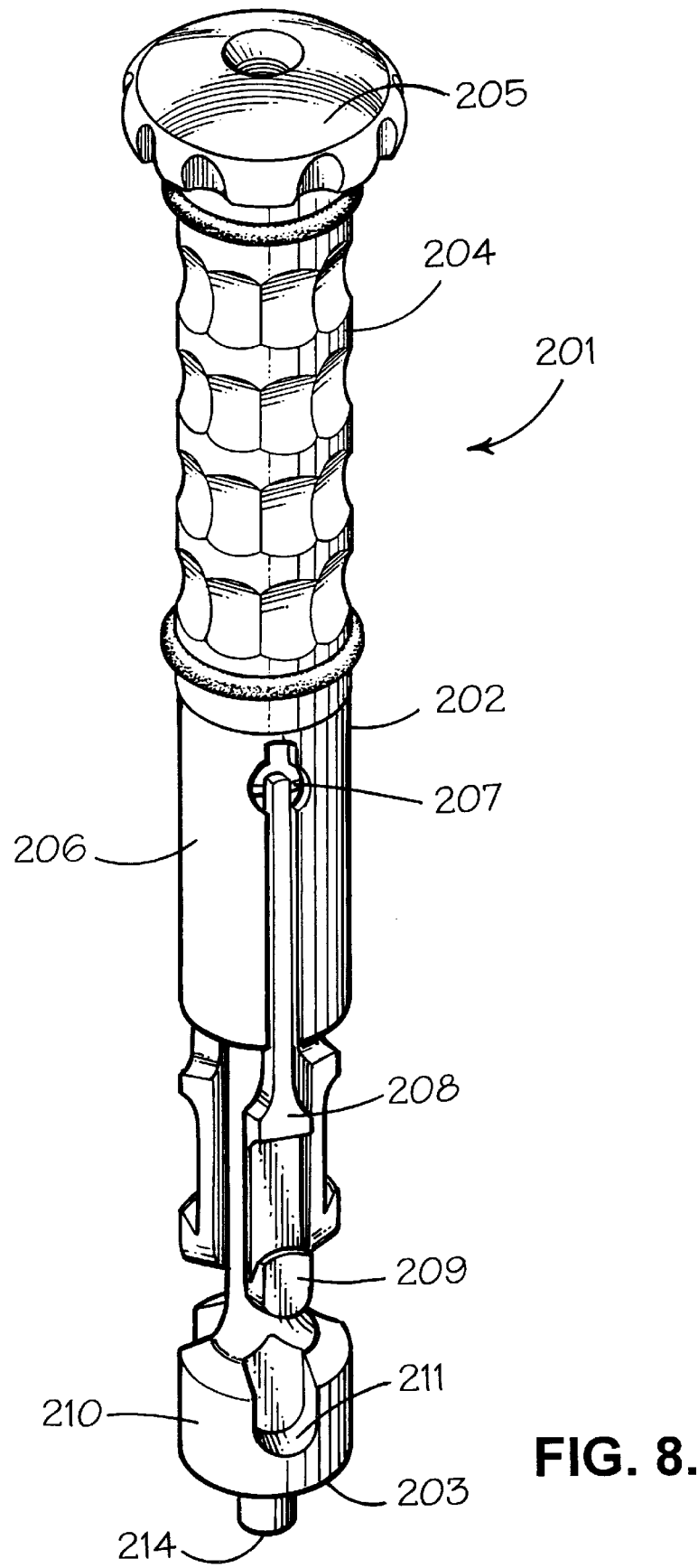
FIG. 8 is an isometric view of a third form of surgical tool in accordance with the invention in its closed condition.

Referring to FIG. 8, there is shown a third form of surgical tool 201 having an elongate hollow body 202 and a first end 203 for engagement with a prosthetic implant. Towards its other end, body 202 has a handle portion 204 which is surmounted by a rotatable knob 205 attached to the upper end of an internally threaded stub shaft (not shown). Below handle portion 204 is a barrel portion 206 within which is slidably located a carriage 207 having an upwardly extending externally threaded projection (not visible in FIG. 8) which is screw threadedly engaged with the internally threaded stub shaft of rotatable knob 205. By rotating knob 205, carriage 207 can be caused to slide axially up or down within barrel portion 206 as desired. At its lower end carriage 207 is provided with an axial bore which receives an upwardly projecting peg mounted in a bottom part 210 of tool 201.

Carriage 207 is provided with three radial slots whose upper ends open into the axial bore in the bottom of carriage 207. In addition each radial slot has associated with it a chordal slot which extends downwardly and inwardly into the carriage 207 so as to provide a pair of bearing surfaces one on either side of each radial slot. Arms 208 having a lower hooked first end 209 are pivotally mounted near their upper ends upon carriage 207 by means of stub members which bear on the bearing surfaces provided by the chordal slots. At a short distance the stub members, each arm 208 is pivotally biased outwardly away from carriage 207 by means of a coil spring trapped between arm 208 and carriage 207. When carriage 207 moves down into barrel portion 206, however, the top of the axial peg in the bottom part 210 impinges upon inward projections on the upper ends of arms 208 so as to cause the arms 208 to swing inwardly until the lower hooked ends 209 are received within cut-out portions 211. On the other hand, as carriage 207 is caused to slide axially up within barrel portion 206, the inward projections on the upper ends of arms 208 no longer impinge on the axial peg within bottom part 210 so that the springs can cause arms 208 to pivot outwardly upon their stub members.

Slots 212 in barrel portion 206 allow this pivoting movement to occur and rounded enlarged portions 213 permit the stub members to pass through during assembly of the tool 201.

At the first end 203 of tool 201 there is an axial peg 214 and an axially offset auxiliary peg 215.

Figure 10:
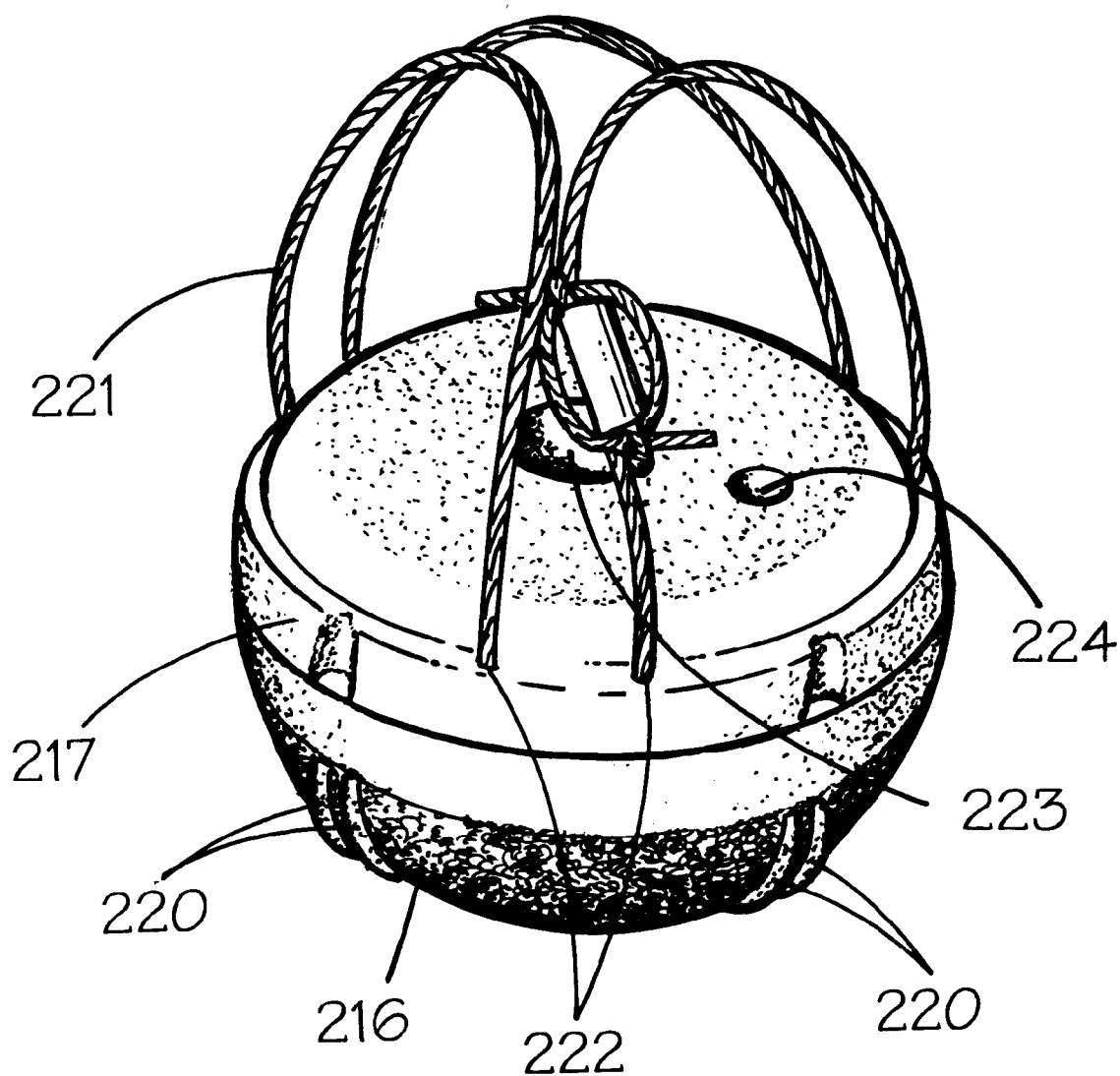
FIG. 10 is a perspective view on a slightly enlarged scale of a further form of prosthetic implant according to the invention for use with the surgical tool of FIGS. 8 and 9.
Figure 11:
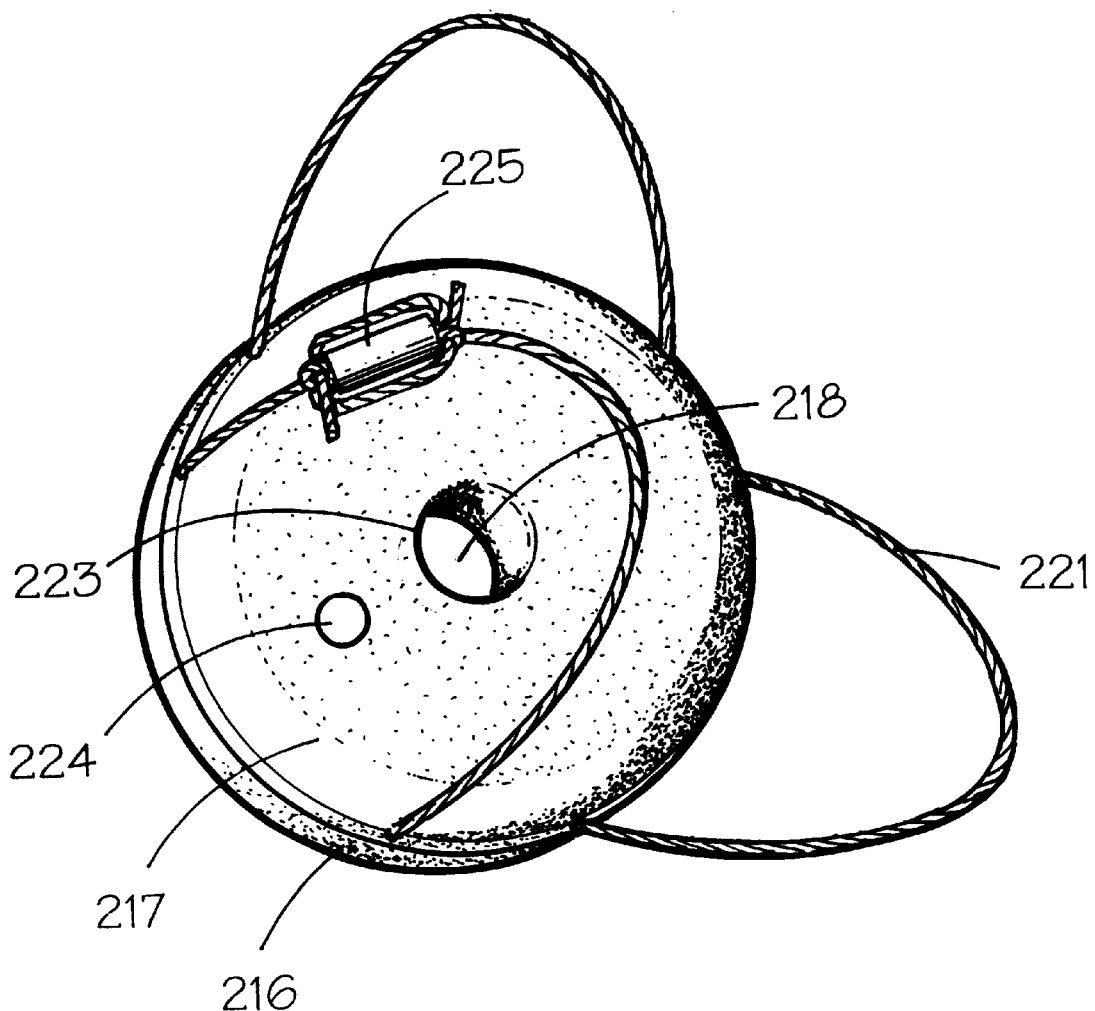
FIG. 11 is a further perspective view, taken, fro, a slightly different angle of the prosthetic implant of FIG. 10.
Figure 12:
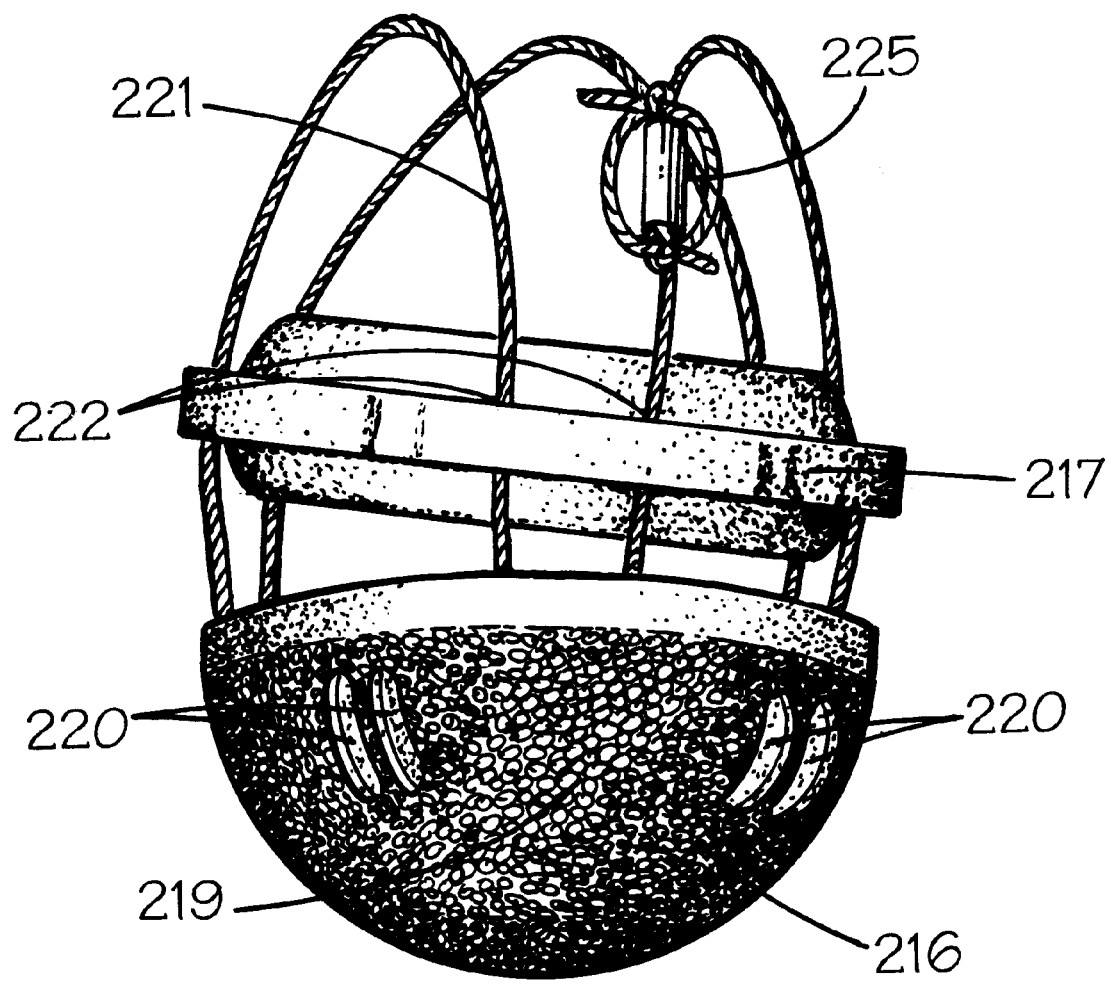
FIG. 12 is a further perspective view of the prosthetic implant of FIGS. 11 and 12 with the protective cover raised.
Figure 13:
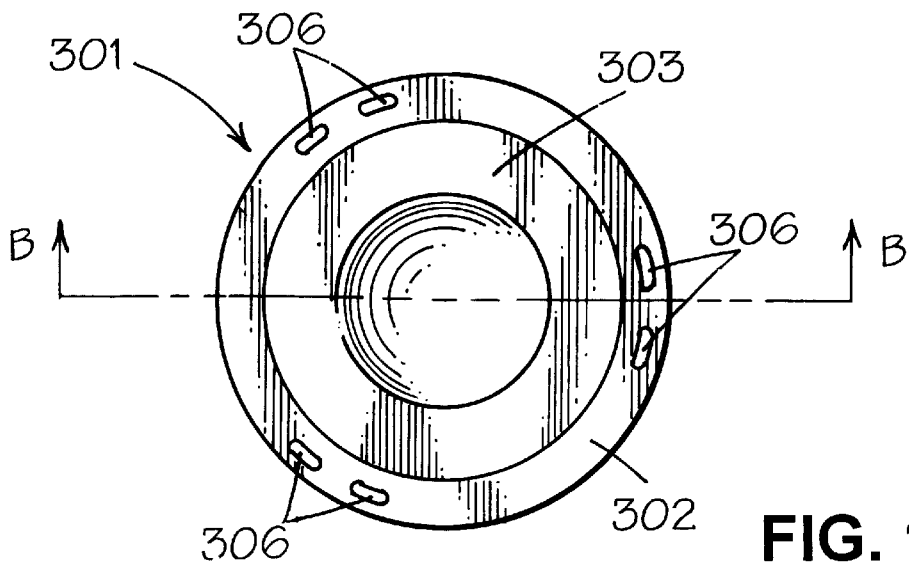
FIG. 13 is a plan view of a further form of prosthetic implant according to the invention.

FIGS. 10 to 12 illustrate an acetabular implant suitable for use with the surgical tool 201. This comprises an acetabular cup 216 and a protective cover 217 made from high density polyethylene. Acetabular cup 216 is made of cobalt chrome with a highly polished inner bearing surface 218 and an outer texturised surface 219 which is intended to promote bone ingrowth following implantation in a patient's hip and which is coated with hydroxyapatite. In addition, the outer surface 219 is provided with two pairs of ribs 220 which are intended to bite into the bone surrounding the patient's acetabular cavity during the implantation operation so as to prevent unwanted rotation of the implant, particularly during the early stages of the post-operative recuperation period.

Protective cover 217 is retained in place on acetabular cup 216 by means of cable 221. This passes through holes 222 in protective cover 217 and through tunnels (not shown) which follow a substantially C-shaped path through the wall of the acetabular cup 216. Protective cover 217 has on its upper side an axial bore 223 to receive peg 214 of surgical tool 201 and also an axially offset bore 224 to receive peg 215 of surgical tool 201.

The ends of cable 221 are secured to one another by means of sleeve 225. As can perhaps best be seen from FIG. 12 a first end portion is threaded upwards through sleeve 225, is then doubled back on itself to form a first loop projecting upwardly from the upper end of sleeve 225 and passed back down through sleeve 225, and is led around sleeve 225, before the first free end is passed through the first loop. In a similar way the other end portion of the cable 221 is passed downwardly through sleeve 225, is doubled back on itself to form a second loop projecting downwardly from the lower end of sleeve 225 and passed back up through sleeve 225, and is led around sleeve 225, before the second free end is passed through the second loop. The four portions of cable passing through sleeve 225 are a snug fit therein. Up applying tension to the cable 221, the first and second loops are tightened and so tighten their grip upon the respective free ends of cable 221 to secure the cable 221 into a continuous loop.

Figure 9:
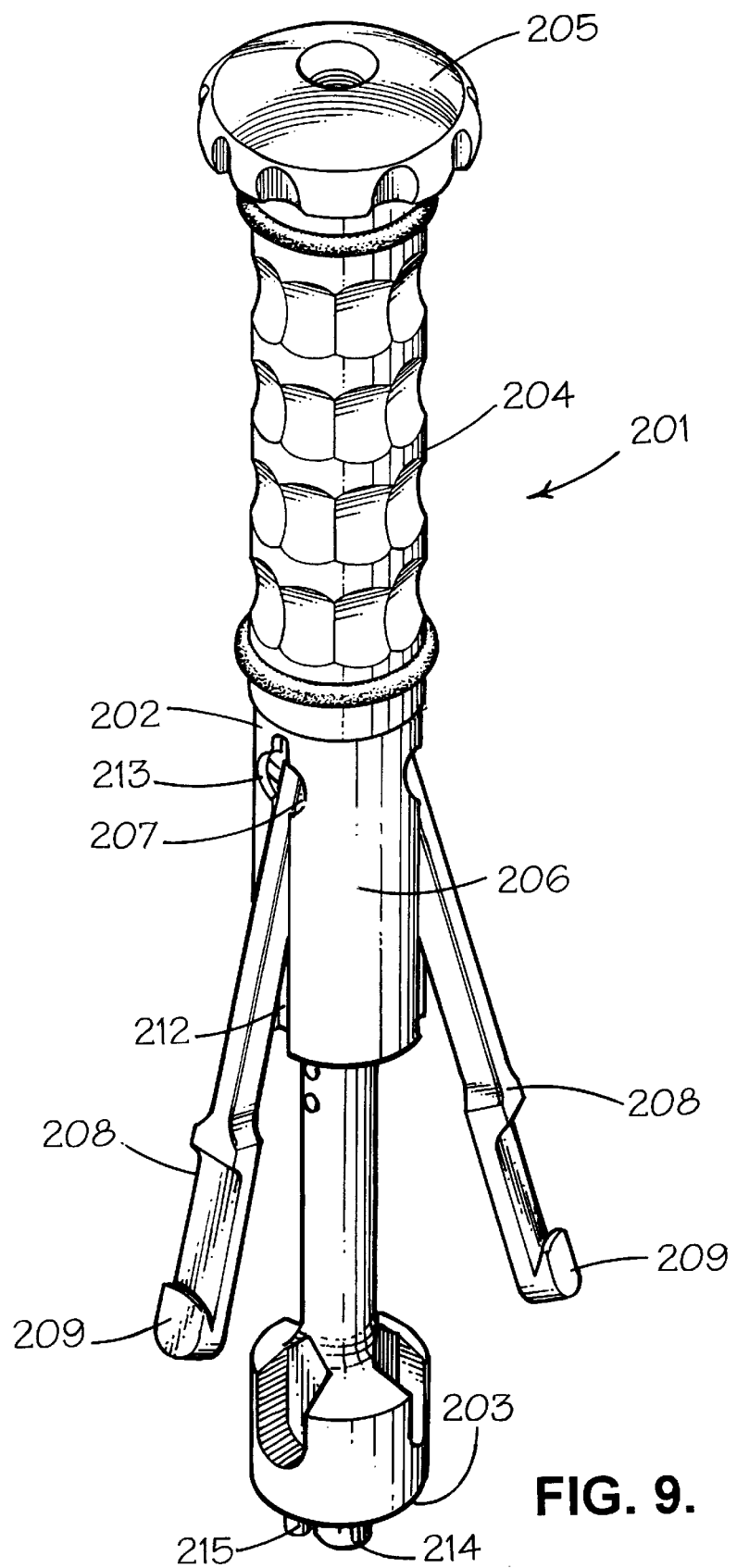
FIG. 9 is an isometric view of the surgical tool of FIG. 8 in its open condition.

In use, a surgeon takes surgical tool 201 with the carriage 207 in its end position nearest end 203 so that arms 208 are fully retracted and fits peg 214 into bore 223 and peg 215 into bore 224. Next he loops the three upstanding loops of cable 221 each over a respective hooked end 209 of an arm 208. He then rotates knob 205 clockwise to cause carriage 207 to slide axially up barrel portion 206. In so doing the upper ends of arms 208 come out of engagement with the axial peg of bottom part 210 and the springs bias arms 208 outwardly towards the position of FIG. 9. In so doing the hooked ends 209 pull upwardly on cable 221 and tighten it.

When the knob can no longer be readily rotated by hand the cable 221 is taut and holds acetabular cup 216 and its protective cover 217 firmly on the end 203 of tool 201.

After the acetabular cup has been seated in the surgically prepared cavity in the patient's hip to the satisfaction of the surgeon, he then rotates knob anticlockwise to move carriage 207 back to its start position, thereby slackening the tension in cable 221 and enabling him to disengage tool 201 from the operative area. When the tool 201 has been removed, he cuts cable 221 and withdraws it from the tunnels in acetabular cup 216 through which it has been threaded and removes protective cover 217 in readiness for insertion of the ball on the patient's femur (or the ball head of a femoral prosthesis) into the acetabular cup 216 and closure of the surgical wound.

Instead of using a stainless steel cable 221 it is alternatively possible to use a synthetic fibrous material of high strength such as Kevlar™ monofilament.

Figure 14:
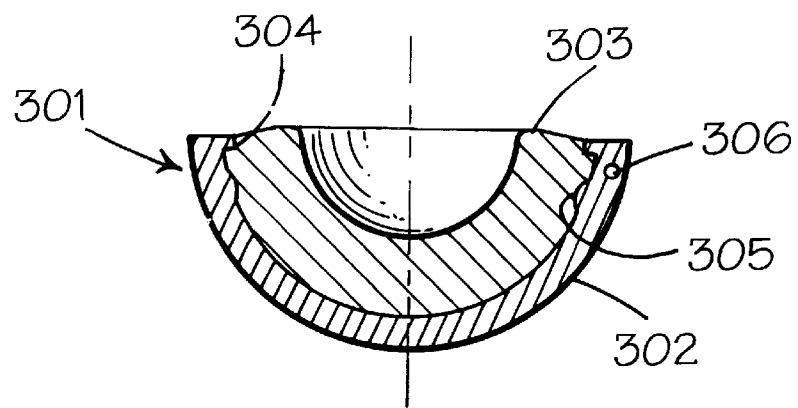
FIG. 14 is a cross section on line B—B of FIG. 13.
Figure 15:
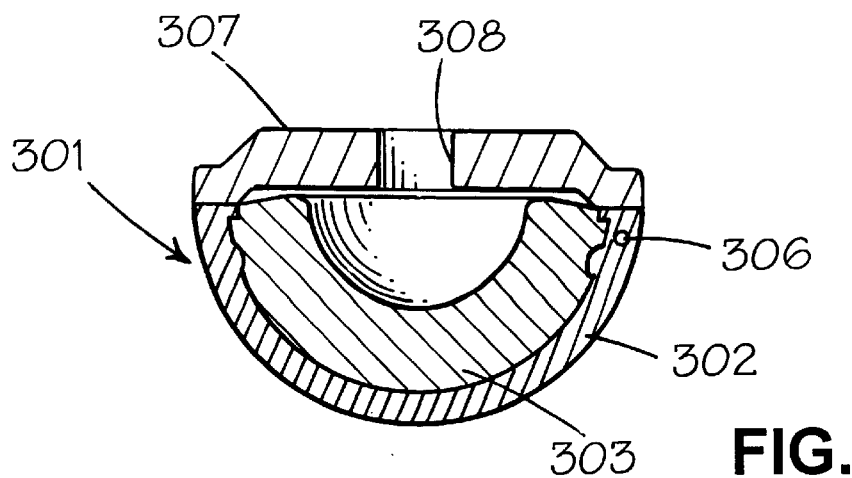
FIG. 15 is a similar cross section to that of FIG. 14 with a protective cover in place to protect the articulating surface of the prosthetic implant of FIGS. 13 and 14.

FIGS. 14 to 16 illustrate another form of acetabular implant 302 according to the invention. This comprises an outer metal cup member 302, which is made, for example, of cobalt chrome, and an inner liner 303 made of high density polyethylene which is intended to provide the bearing surface of the ball head of a femoral prosthesis. Surrounding the upper rim of the inner surface of cup-member 302 is an inwardly projecting lip 304 below which is an adjacent circumferential ridge 305. Inner liner 303 has a peripheral ledge on its upper face which substantially conforms in dimensions to lip 304. It also has a circumferential groove corresponding to ridge 305. Liner 303 is press fitted in the factory into acetabular cup member 302 with the circumferential ledge on liner 303 engaged under the lip 304 and with ridge 305 engaged in the corresponding circumferential groove in liner 303.

Three short tunnels 306 each of which follows a generally C-shaped path are formed between the three adjacent pairs of tunnel openings which are visible in FIG. 14. These tunnels are provided for the passage of a closed loop of cable, similar to cable 221, for retaining a protective cover 307 which is intended to protect the inner surface of liner 303 during implantation by a surgeon. This protective cover 307 has an axial bore 308, similar to bore 223 of protective cover 217, and also an axially offset bore (not shown) similar to bore 224 of protective cover 217, to enable the implant 301 to be used with the surgical tool 201.

Instead of using one continuous loop of cable 221, it is alternatively possible to use three separate continuous loops of cable or Kevlar™ monofilament, one for each tunnel 306.

What is claimed is:

1. A prosthetic implant for implantation into a surgically prepared cavity in a bone of a patient comprising a main body portion, having a first surface shaped for presentation to a reception bone surface of the surgically prepared cavity and a second surface shaped for receipt of an articulating joint, and filamentary member attachment means adapted for attachment of a filamentary member to the implant comprising a bore in the main body portion through which a filamentary member can be threaded, the filamentary member attachment means comprising a plurality of bores in the main body portion and wherein a filamentary member having a pair of free ends is threaded through each of the plurality of bores in turn, the free ends of the filamentary member being secured one to another so as to form a closed loop of filamentary member.

2. A prosthetic implant according to claim 1, wherein the free ends of the filamentary member are secured to one another by means of a sleeve having first and second ends, the sleeve snugly receiving a first looped portion of filamentary member located near a first end portion of the filamentary member and inserted from the first end of the sleeve so as to project as a first loop from the second end of the sleeve with the first end portion being passed through the first loop, and the sleeve further snugly receiving a second looped portion of filamentary member located near a second end portion of the filamentary member and inserted from the second end of the sleeve so as to project as a second loop from the first end of the sleeve with the second end portion being passed through the second loop, whereby upon tension being applied to the closed loop of filamentary member the first and second end portions of the filamentary member are firmly gripped by the first and second loops respectively.

3. A prosthetic implant according to claim 1, wherein the filamentary member is a poly-filament cable.

4. A prosthetic implant comprising a main body portion, having a first surface shaped for presentation to a surgically prepared bone cavity of a patient and a second surface shaped for receipt of an articulating joint, and filamentary member attachment means adapted for attachment of a filamentary member to the implant comprising a plurality of bores in the main body portion through which a filamentary member can be threaded, a filamentary member having a pair of free ends is threaded through each of the plurality of bores in turn, the free ends of the filamentary member being secured one to another so as to form a closed loop of filamentary member, the free ends of the filamentary member being secured to one another by means of a sleeve having first and second ends, the sleeve snugly receiving a first looped portion of filamentary member located near a first end portion of the filamentary member and inserted from the first end of the sleeve so as to project as a first loop from the second end of the sleeve with the first end portion being passed through the first loop, and the sleeve further snugly receiving a second looped portion of filamentary member located near a second end portion of the filamentary member and inserted from the second end of the sleeve so as to project as a second loop from the first end of the sleeve with the second end portion being passed through the second loop, whereby upon tension being applied to the closed loop of filamentary member the first and second loops are tightened and the first and second end portions of the filamentary member are firmly gripped by the first and second loops respectively.

5. A prosthetic implant according to claim 4, wherein the filamentary member is a poly-filament cable.

6. An acetabular hip prosthesis for implantation in a surgically prepared socket in a hip of a patient comprising:
  a generally cup-shaped body having:
    an outer generally convex surface for contact with bone of a surgically prepared socket in a hip of a patient;
    an inner generally concave surface;
    a peripheral bridge portion whose surface extends between the outer generally convex surface and the inner generally concave surface; and
    at least one bore which extends from a first opening in the surface of the bridge portion through an interior portion of the generally cup-shaped body to a second opening in the surface of the bridge portion, the bore being adapted for receipt of a filamentary member therethrough for holding the prosthesis on the end of an insertion tool to facilitate insertion of the prosthesis into the prepared socket.

7. An acetabular hip prosthesis according to claim 6, wherein a filamentary member having a pair of free ends is threaded through said at least one bore, the free ends of the filamentary member being secured one to another so as to form a closed loop of filamentary member by means of a sleeve having first and second ends, the sleeve snugly receiving a first looped portion of filamentary member located near a first end portion of the filamentary member and inserted from the first end of the sleeve so as to project as a first loop from the second end of the sleeve with the first end portion being passed through the first loop, and the sleeve further snugly receiving a second looped portion of filamentary member located near a second end portion of the filamentary member and inserted from the second end of the sleeve so as to project as a second loop from the first end of the sleeve with the second end portion being passed through the second loop, whereby upon tension being applied to the closed loop of filamentary member the first and second loops are tightened and the first and second end portions of the filamentary member are firmly gripped by the first and second loops respectively.

8. An acetabular hip prosthesis for implantation in a surgically prepared socket in a hip of a patient comprising:
   a generally cup-shaped body having:
      an outer generally convex surface for contact with bone of a surgically prepared socket in a hip of a patient;
      an inner generally concave surface;
      a peripheral bridge portion whose surface extends between the outer generally convex surface and the inner generally concave surface; and
      a plurality of bores each of which extends from a first opening in the surface of the bridge portion through an interior portion of the generally cup-shaped body to a second opening in the surface of the bridge portion, the bore being adapted for receipt of a filamentary member therethrough for holding the prosthesis on the end of an insertion tool to facilitate insertion of the prosthesis into the prepared socket.

9. An acetabular hip prosthesis according to claim 8, wherein the outer generally convex surface of the cup-shaped body is provided with a coating of hydroxyapatite.

10. An acetabular hip prosthesis according to claim 8, wherein the outer generally convex surface of the cup-shaped body is texturised to facilitate ingrowth of bone after implantation into a surgically prepared hip socket of a patient.

11. An acetabular hip prosthesis according to claim 8, wherein a filamentary member having a pair of free ends is threaded through said plurality of bores, the free ends of the filamentary member being secured one to another so as to form a closed loop of filamentary member.

12. An acetabular hip prosthesis according to claim 11, wherein the free ends of the filamentary member are secured to one another by means of a sleeve having first and second ends, the sleeve snugly receiving a first looped portion of filamentary member located near a first end portion of the filamentary member and inserted from the first end of the sleeve so as to project as a first loop from the second end of the sleeve with the first end portion being passed through the first loop, and the sleeve further snugly receiving a second looped portion of the filamentary member located near a second end portion of the filamentary member and inserted from the second end of the sleeve so as to project as a second loop from the first end of the sleeve with the second end portion being passed through the second loop, whereby upon tension being applied to the closed loop of filamentary member the first and second loops are tightened and the first and second end portions of the filamentary member are firmly gripped by the first and second loops respectively.

13. A protected prosthetic implant comprising a main body portion, having a first surface for presentation to a receptive bone surface and a second surface for receipt of an articulating joint, filamentary member attachment means adapted for attachment of a filamentary member to the implant, said filamentary member attachment means comprising at least one element selected from a lug on the main body portion and a bore in the main body portion and a protective cap for covering at least part of the second surface of the main body portion of the implant, the protective cap being attached to the main body portion of the implant by means of a cable.

14. A protected prosthetic implant according to claim 13, wherein the cable is tensioned so that the protective cap is tightly attached to the main body portion of the implant.

15. A protected prosthetic implant according to claim 13, wherein the protective cap is of a rigid material.

16. A protected prosthetic implant according to claim 13 wherein the protective cap is a disposable protective cap.

17. A protected prosthetic implant according to claim 13, wherein the protective cap is reusable after appropriate sterilisation.

18. A protected prosthetic implant comprising a main body portion, having a first surface for presentation to a receptive bone surface and a second surface for receipt of an articulating joint, filamentary member attachment means adapted for attachment of a filamentary member to the implant, said filamentary member attachment means comprising at least one element selected from a lug on the main body portion and a bore in the main body portion and a protective cap for covering at least part of the second surface of the main body portion of the implant, the protective cap being provided with a number of holes adapted to threadably receive the filamentary member therethrough for a attachment of the protective cap to the prosthetic implant.

19. A protected prosthetic implant according to claim 18, wherein the protective cap is a disposable protective cap.

20. A protected prosthetic implant according to claim 18, wherein the protective cap is reusable after appropriate sterilisation.

21. A protected prosthetic implant according to claim 18, wherein the protective cap is of a rigid material.

22. A protected acetabular hip prosthesis for implantation in a surgically prepared socket in a hip of a patient comprising:
   (i) a generally cup-shaped metal body having:
      an outer generally convex surface for contact with bone of a surgically prepared socket in a hip of a patient;
      an inner substantially part spherical cavity in the metal body, the cavity having a generally concave polished surface for receipt of a ball head on a femoral prosthesis and a periphery surrounding the cavity and defining a mouth;
      a peripheral bridge portion whose surface extends between the periphery of the cavity and the outer generally convex surface; and
      at least one bore which extends from a first opening in the surface of the peripheral bridge portion through an interior portion of the generally cup-shaped body to a second opening in the surface of the bridge portion, the at least one bore being adapted for receipt of a filamentary member therethrough for holding the prosthesis on the end of an insertion tool to facilitate insertion of the prosthesis into the surgically prepared socket;
   (ii) a cover member adapted to bridge the cavity, the cover having apertures therethrough which correspond to the first and second openings in the metal body and are adapted for passage of the filamentary member; and (iii) a filamentary member having a pair of free ends threaded through the at least one bore in the generally cup-shaped metal body and through the apertures in the cover member, the free ends of the filamentary member being secured one to another to form a closed loop a filamentary member which secures the cover to the generally cup-shaped metal body.

23. A protected acetabular hip prosthesis according to claim 31, wherein the free ends of the filamentary member are secured to one another by means of a sleeve having first and second ends, the sleeve snugly receiving a first looped portion of filamentary member located near a first end portion of the filamentary member and inserted from the first end of the sleeve so as to project as a first loop from the second end of the sleeve with the first end portion being passed through the first loop, and the sleeve further snugly receiving a second looped portion of filamentary member located near a second end portion of the filamentary member and inserted from the second end of the sleeve so as to project as a second loop from the first end of the sleeve with the second end portion being passed through the second loop, whereby upon tension being applied to the closed loop of filamentary member the first and second end portions of the filamentary member are firmly gripped by the first and second loops respectively.

24. A protected acetabular hip prosthesis for implanation in a surgically prepared socket in a hip of a patient comprising:

(i) a generally cup-shaped metal body having:
an outer generally convex surface for contact with bone of a surgically prepared socket in a hip of a patient;
an inner substantially part spherical cavity in the metal body, the cavity having a generally concave polished surface for receipt of a ball head on a femoral prosthesis and a periphery surrounding the cavity and defining a mouth;
a peripheral bridge portion whose surface extends between the periphery of the cavity and the outer generally convex surface; and
a plurality of bores each of which extends from a first opening in the surface of the peripheral bridge portion through an interior portion of the generally cup-shaped body to a second opening in the surface of the bridge portion, the bores being adapted for receipt of a filamentary member therethrough for holding the prosthesis on the end of an insertion tool to facilitate insertion of the prosthesis into the surgically prepared socket;

(ii) a cover member adapted to bridge the cavity, the cover having apertures therethrough which correspond to the first and second openings in the generally cup-shaped metal body and are adapted for passage of the filamentary member; and (iii) a filamentary member having a pair of free ends threaded through each of the plurality of holes in the generally cup-shaped metal body and through the apertures in the cover member, the free ends of the filamentary member being secured one to another to form a closed loop of filamentary member which secures the cover to the generally cup-shaped metal body.

25. A protected acetabular hip prosthesis according to claim 24, wherein the outer generally convex surface of the cup-shaped metal body is provided with a coating of hydroxyapatite.

26. A protected acetabular hip prosthesis according to claim 24, wherein the outer generally convex surface of the cup-shaped metal body is texturised to facilitate ingrowth of bone after implantation into a surgically prepared hip socket of a patient.

27. A protected acetabular hip prosthesis according to claim 24, wherein the free ends of the filamentary member are secured to one another by means of a sleeve having first and second ends, the sleeve snugly receiving a first looped portion of filamentary member located near a first end portion of the filamentary member and inserted from the first end of the sleeve so as to project as a first loop from the second end of the sleeve with the first end portion being passed through the first loop, and the sleeve further snugly receiving a second looped portion of filamentary member located near a second end portion of the filamentary member and inserted from the second end of the sleeve so as to project as a second loop from the first end of the sleeve with the second end portion being passed through the second loop, whereby upon tension being applied to the closed loop of filamentary member the first and second loops are tightened and the first and second end portions of the filamentary member are firmly gripped by the first and second loops respectively.

28. A protected acetabular hip prosthesis for implantation in a surgically prepared socket in a hip of a patient comprising:

(i) a generally cup-shaped metal body having:
an outer generally convex surface for contact with bone of a surgically prepared socket in a hip of a patient;
a cavity in the metal body for receipt of a liner of plastics material, the cavity having a periphery surrounding the cavity and defining a mouth;
a peripheral bridge portion whose surface extends between the periphery of the cavity and the outer generally convex surface; and
a plurality of bores each of which extends from a first opening in the surface of the peripheral bridge portion through an interior portion of the generally cup-shaped metal body to a second opening in the surface of the bridge portion, the bores being adapted for receipt of a filamentary member therethrough for holding the prosthesis on the end of an insertion tool to facilitate insertion of the prosthesis into the surgically prepared socket;

(ii) a liner of plastics material secured in the cavity of the generally cup-shaped metal body, the liner having an outer surface adapted to conform to the inner surface of the cavity in the generally cup-shaped metal body and a substantially part spherical inner surface for receipt of a ball head on a femoral hip prosthesis;

(iii) a cover member having a first face adapted to bridge the cavity, the cover member having apertures therethrough which correspond to the first and second openings in the generally cup-shaped metal body and are adapted for passage of the filamentary member; and (iv) a filamentary member having a pair of free ends threaded through each of the plurality of bores in the generally cup-shaped metal body and through the apertures in the cover member, the free ends of the filamentary member being secured one to another to form a closed loop of filamentary member which secures the cover to the generally cup-shaped metal body.

29. A protected acetabular hip prosthesis according to claim 28, wherein the outer generally convex surface of the cup-shaped metal body is provided with a coating of hydroxyapatite.

30. A protected acetabular hip prosthesis according to claim 28, wherein the outer generally convex surface of the cup-shaped metal body is texturised to facilitate ingrowth of bone after implantation into a surgically prepared hip socket of a patient.

31. A protected acetabular hip prosthesis according to claim 37, wherein the free ends of the filamentary member are secured to one another by means of a sleeve having first and second ends, the sleeve snugly receiving a first looped portion of filamentary member located near a first end portion of the filamentary member and inserted from the first end of the sleeve so as to project as a first loop from the second end of the sleeve with the first end portion being passed through the first loop, and the sleeve further snugly receiving a second looped portion of filamentary member located near a second end portion of the filamentary member and inserted from the second end of the sleeve so as to project as a second loop from the first end of the sleeve with the second end portion being passed through the second loop, whereby upon tension being applied to the closed loop of filamentary member the first and second loops are tightened and the first and second end portions of the filamentary member are firmly gripped by the first and second loops respectively.

32. A protected acetabular hip prosthesis according to claim 28, wherein the cavity in the cup-shaped metal body is provided with an inwardly projecting lip surrounding the mouth of the cavity and in which the liner is provided with a peripheral ledge which is adapted to snap fit under the inwardly projecting lip of the cup-shaped metal body.

33. A protected acetabular hip prosthesis according to claim 32, wherein the cavity in the cup-shaped metal body is provided with a circumferential internal ridge below and adjacent the inwardly projecting lip and wherein the liner is provided with a corresponding circumferential groove on its outer surface which is adapted to receive the circumferential ridge.

34. A protected acetabular hip prosthesis according to claim 28, wherein the liner is made from high density polyethylene.

35. A protected acetabular hip prosthesis according to claim 28, wherein the cover member is provided on a second face opposite its first face with an axial blind bore for location of a corresponding axial locating peg on an insertion tool.

36. A protected acetabular hip prosthesis according to claim 35, wherein the cover member is provided on its second face with an auxiliary bore whose axis is parallel to and offset from the axis of the axial blind bore, the auxiliary bore being adapted to receive a corresponding offset peg on an insertion tool to prevent relative rotation of the acetabular hip prosthesis and cover member about the axis of the axial locating peg of the insertion tool.

37. A prosthetic implant comprising a main body portion, having a first surface for presentation to a receptive bone surface and a second surface for receipt of an articulating joint, filamentary member attachment means adapted for attachment of a filamentary member to the implant comprising a plurality of bores in the main body portion, and a filamentary member having a pair of free ends and threaded through each of the plurality of bores in turn, the free ends of the filamentary member being secured one to another so as to form a closed loop of filamentary member by means of a sleeve having first and second ends, the sleeve snugly receiving a first looped portion of filamentary member located near a first end portion of the filamentary member and inserted from the first end of the sleeve so as to project as a first loop from the second end of the sleeve with the first end portion being passed through the first loop, and the sleeve further snugly receiving a second looped portion of filamentary member located near a second end portion of the filamentary member and inserted from the second end of the sleeve so as to project as a second loop from the first end of the sleeve with the second end portion being passed through the second loop, whereby upon tension being applied to the closed loop of filamentary member the first and second end portions of the filamentary member are firmly gripped by the first and second loops respectively.

38. A prosthetic implant comprising a main body portion, having a first surface for presentation to a surgically prepared bone cavity of a patient and a second surface for receipt of an articulating joint, filamentary member attachment means adapted for attachment of a filamentary member to the implant comprising a plurality of bores in the main body portion, and a filamentary member having a pair of free ends and threaded through each of the plurality of bores in turn, the free ends of the filamentary member being secured one to another so as to form a closed loop of filamentary member by means of a sleeve having first and second ends, the sleeve snugly receiving a first looped portion of filamentary member located near a first end portion of the filamentary member and inserted from the first end of the sleeve so as to project as a first loop from the second end of the sleeve with the first end portion being passed through the first loop, and the sleeve further snugly receiving a second looped portion of filamentary member located near a second end portion of the filamentary member and inserted from the second end of the sleeve so as to project as a second loop from the first end of the sleeve with the second end portion being passed through the second loop, whereby upon tension being applied to the closed loop of filamentary member the first and second loops are tightened and the first and second end portions of the filamentary member are firmly gripped by the first and second loops respectively.

39. A protected implant comprising a main body portion, having a first surface for presentation to a receptive bone surface and a second surface for receipt of an articulating joint, filamentary member attachment means adapted for attachment of a filamentary member to the implant, and a protective cap for covering at least part of the second surface of the main body portion of the implant attached to the main body portion of the implant by means of a cable.

40. A protected prosthetic implant according to claim 39 wherein the cable is tensioned so that the protective cap is tightly attached to the main body portion of the implant.

41. A prosthetic implant for implantation into a surgically prepared cavity in a bone of a patient comprising a main body portion, having a first surface shaped for presentation to a receptive bone surface of the surgically prepared cavity and a second surface shaped for receipt of an articulating joint, filamentary member attachment means adapted for attachment of a filamentary member to the implant comprising a bore in the main body portion through which a filamentary member can be threaded, and a cable temporarily attached to the main body portion of the implant by the filamentary member attachment means.

42. A prosthetic implant according to claim 41, wherein the filamentary member attachment means comprises a lug on the main body portion around which the cable can be looped.

43. A prosthetic acetabular implant comprising a main body portion, having a first surface shaped for presentation to a receptive pelvic bone surface and a second surface shaped for receipt of an articulating joint, and filamentary member attachment means adapted for attachment of a filamentary member to the implant comprising a plurality of equally sized lugs integrally formed with the main body portion which are spaced substantially evenly around the main body portion of the implant whereby a filamentary member can be looped around each of the plurality of lugs for holding the implant on the end of an insertion tool to facilitate presentation of the implant to the pelvic bone surface.

44. A prosthetic acetabular implant according to claim 43, wherein the outer generally convex surface of the cup-shaped body is provided with a coating of hydroxyapatite.

45. A prosthetic acetabular implant according to claim 43, wherein the outer generally convex surface of the cup-shaped body is texturised to facilitate ingrowth of bone after implantation into a surgically prepared hip socket of a patient.

46. A prosthetic acetabular implant according to claim 43, further comprising a protective cap attached to the main body portion of the implant by means of a cable.

47. A prosthetic acetabular implant according to claim 46, wherein the cable is tensioned so that the protective cap is tightly attached to the main body portion of the implant.

48. A prosthetic acetabular implant according to claim 46, wherein the protective cap is of a rigid material.

49. A prosthetic acetabular implant according to claim 46, wherein the protective cap is provided with a number of holes, through which a filamentary member is threaded for attachment of the protective cap to the implant.

50. A prosthetic acetabular implant according to claim 43, further comprising a cable temporarily attached to the main body portion of the implant by the filamentary member attachment means.

51. An acetabular hip prosthesis for implantation in a surgically prepared socket in a hip of a patient comprising:
   a generally cup-shaped body having:
      an outer generally convex surface for contact with bone of a surgically prepared socket in a hip of a patient; and
      an inner generally concave surface; and
      a peripheral bridge portion whose surface extends between the outer generally convex surface and the inner generally concave surface and defines an outer rim at its junction with the outer generally convex surface;
   wherein a plurality of portions of the generally outer convex surface are removed to form a plurality of external undercut lugs which are substantially evenly spaced around the outer rim and are each adapted to receive a portion of a filamentary member looped therearound for holding the prosthesis on the end of an insertion tool to facilitate insertion of the prosthesis into the prepared socket.

52. An acetabular hip prosthesis according to claim 51, wherein the outer generally convex surface of the cup-shaped body is provided with a coating of hydroxyapatite.

53. An acetabular hip prosthesis according to claim 51, wherein the outer generally convex surface of the cup-shaped body is texturised to facilitate ingrowth of bone after implantation into a surgically prepared hip socket of a patient.

54. An acetabular hip prosthesis according to claim 51, further comprising a protective cap attached to the main body portion of the implant by means of a cable.

55. An acetabular hip prosthesis according to claim 54, wherein the cable is tensioned so that the protective cap is tightly attached to the main body portion of the implant.

56. An acetabular hip prosthesis according to claim 54, wherein the protective cap is of a rigid material.

57. An acetabular hip prosthesis according to claim 54, wherein the protective cap is provided with a number of holes, through which a filamentary member is threaded for attachment of the protective cap to the implant.

58. An acetabular hip prosthesis according to claim 51, further comprising a cable temporarily attached to the main body portion of the implant by the filamentary member attachment means.

59. An acetabular hip prosthesis for implantation in a surgically prepared socket in a hip of a patient comprising:
   a generally cup-shaped body having:
      an outer generally convex surface defining an external envelope, the outer generally convex surface being shaped for contact with bone of a surgically prepared socket in a hip of a patient; and
      an inner generally concave surface; and
      a peripheral bridge portion whose surface extends between the outer generally convex surface and the inner generally concave surface and defines an outer rim at its junction with the outer generally convex surface;
   wherein a plurality of portions of the generally outer convex surface are removed from within the external envelope so as to form a plurality of external undercut lugs which are substantially evenly spaced around the outer rim and are each adapted to receive a respective portion of a filamentary member looped therearound for holding the prosthesis on the end of an insertion tool to facilitate insertion of the prosthesis into the prepared socket.

60. An acetabular hip prosthesis according to claim 59, wherein the outer generally convex surface of the cup-shaped body is provided with a coating of hydroxyapatite.

61. An acetabular hip prosthesis according to claim 59, wherein the outer generally convex surface of the cup-shaped body is texturised to facilitate ingrowth of bone after implantation into a surgically prepared hip socket of a patient.

62. An acetabular hip prosthesis according to claim 59, further comprising a protective cap attached to the main body portion of the implant by means of a cable.

63. An acetabular hip prosthesis according to claim 62, wherein the cable is tensioned so that the protective cap is tightly attached to the main body portion of the implant.

64. An acetabular hip prosthesis according to claim 62, wherein the protective cap is of a rigid material.

65. An acetabular hip prosthesis according to claim 59, wherein the protective cap is provided with a number of holes, through which a filamentary member is threaded for attachment of the protective cap to the implant.

* * * * *